(12) United States Patent
Han et al.

(10) Patent No.: US 6,723,514 B2
(45) Date of Patent: Apr. 20, 2004

(54) COMPOSITIONS AND METHODS FOR DIRECTLY AND RAPIDLY ANALYZING THE BIOCHEMICAL COMPONENTS OF MICROORGANISMS

(75) Inventors: Sean Xiaoliang Han, San Francisco, CA (US); Wan-Heng Wang, Grapevine, TX (US)

(73) Assignee: Biochaiv Institute, Inc., Hayward, CA (US)

( * ) Notice: Subject to any disclaimer, the term of this patent is extended or adjusted under 35 U.S.C. 154(b) by 0 days.

(21) Appl. No.: 09/906,867

(22) Filed: Jul. 16, 2001

(65) Prior Publication Data

US 2002/0022230 A1 Feb. 21, 2002

Related U.S. Application Data

(63) Continuation of application No. 09/221,762, filed on Dec. 28, 1998, now Pat. No. 6,265,164.
(60) Provisional application No. 60/079,506, filed on Mar. 26, 1998.

(51) Int. Cl.[7] .............................................. C07H 21/04
(52) U.S. Cl. ................................................. 435/6; 435/5
(58) Field of Search ............................................ 435/6, 5

(56) References Cited

U.S. PATENT DOCUMENTS

| | | | |
|---|---|---|---|
| 5,595,876 A | * | 1/1997 | Rakestraw ..................... 435/6 |
| 5,726,021 A | | 3/1998 | Britschgi et al. ............... 435/6 |
| 5,766,863 A | | 6/1998 | Godowski et al. .......... 435/7.21 |
| 6,265,164 B1 | * | 7/2001 | Han et al. ...................... 435/6 |

OTHER PUBLICATIONS

Liu et al. (BioTechniques, vol. 18, No. 2, p. 214–217, 1995.*
Ausubel, F.M. et al., *Current Protocols in Molecular Biology*, vol. 2, John Wiley & Sons, New York: p. 1–16–1–17 (1989).
Biao, L. et al., *Bio Techniques* 23:601–607 (1997).
Costa, G.I. et al., "ScreenTest™ Recombinant screening in One day,", *Strategies*, 7:35–37 (1994).
Sambrook, J. et al., *Molecular Cloning: A Laboratory Manual*, 2nd. Ed. CSH Laboratory Press. Cold Spring Harbor, NY. 1.25–1.30, 1.32, B.22 (1989).
Poh et al., "Rapid In Situ Generation of DNA Restriction Endonuclease Patterns for *Neisseria gonorrhoeae*," *J Clin Microbiol* (Dec. 1989) 27(12):2784–2788.

* cited by examiner

*Primary Examiner*—W. Gary Jones
*Assistant Examiner*—Juliet C. Switzer
(74) *Attorney, Agent, or Firm*—Chi Ping Chang; Pacific Law Group LLP

(57) ABSTRACT

This invention concerns novel methods and compositions useful for directly and rapidly analyzing the biochemical components of microorganisms. The compositions and methods of the present invention obviate the need for extracting and purifying the biochemicals prior to analysis.

14 Claims, 6 Drawing Sheets

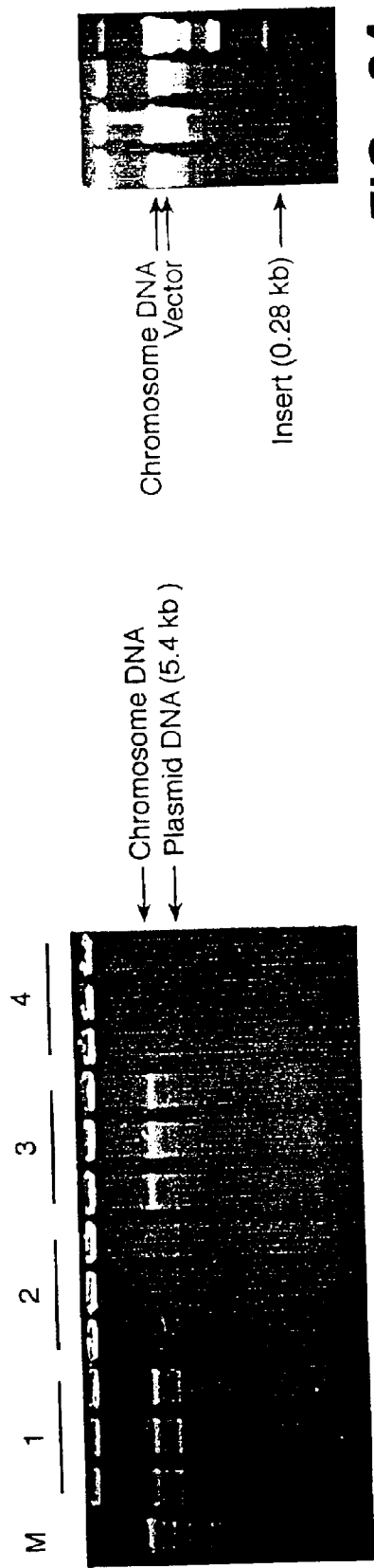
FIG._1
FIG._2A
FIG._2B
FIG._2C
FIG._2D
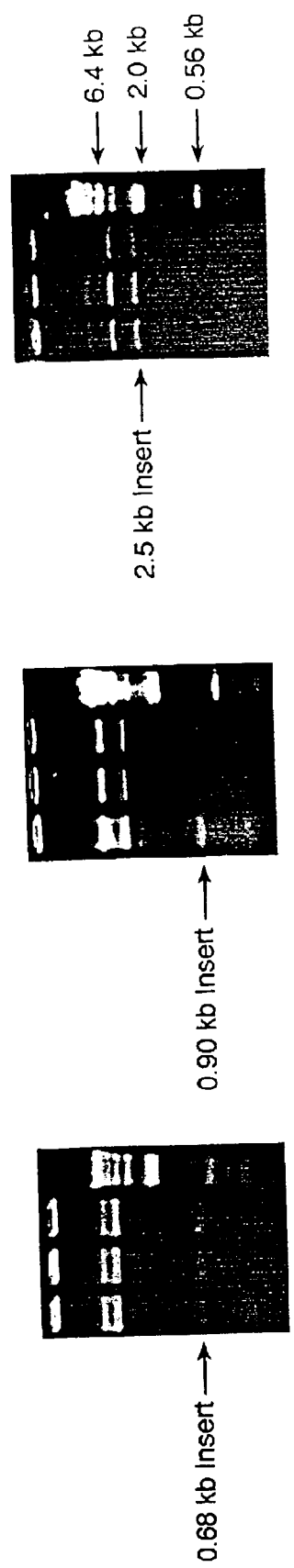

FIG._3
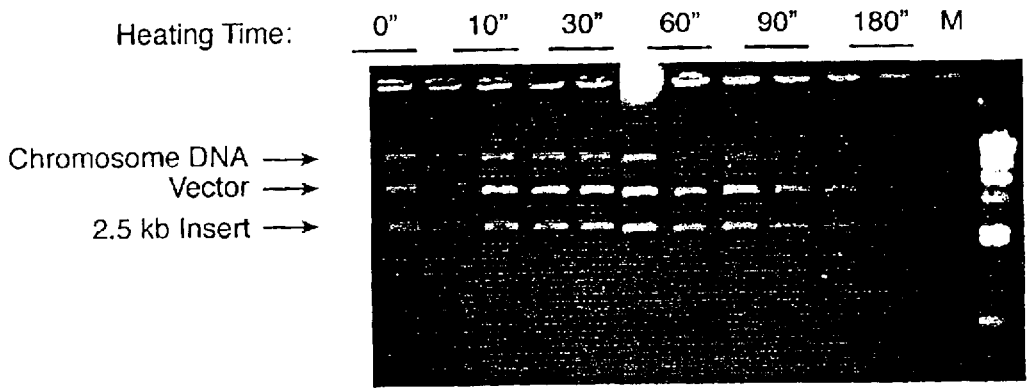
FIG._5
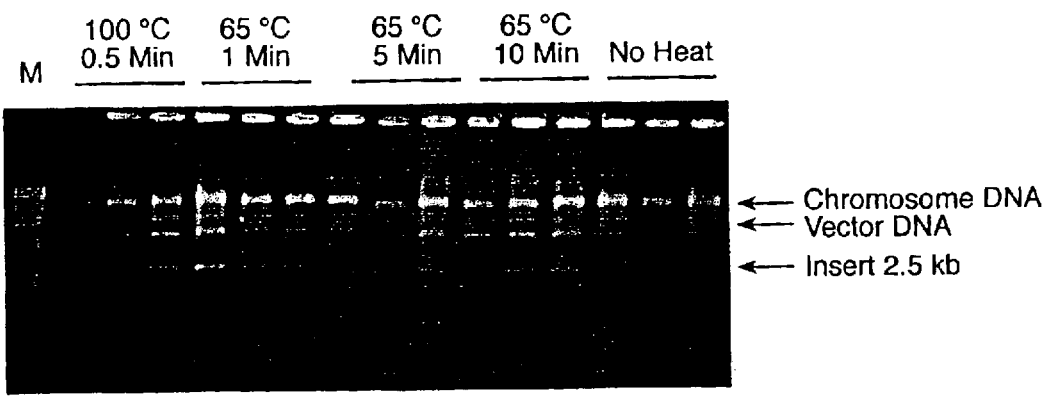
FIG._6

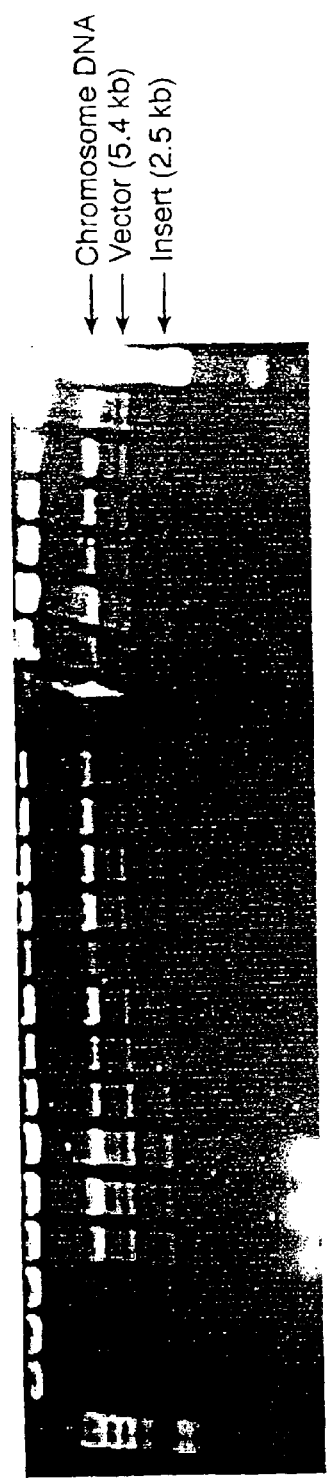
FIG._4
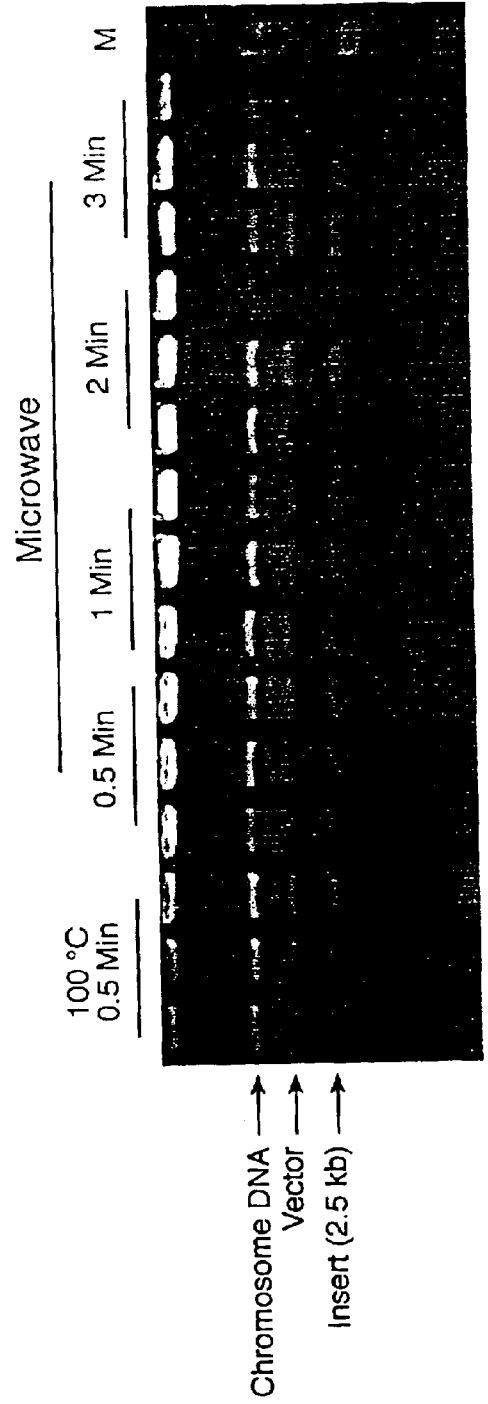
FIG._7

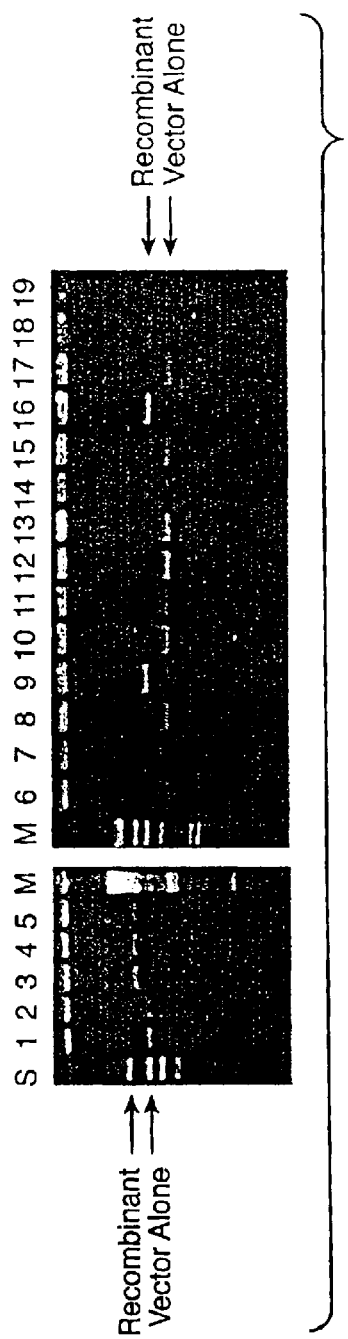
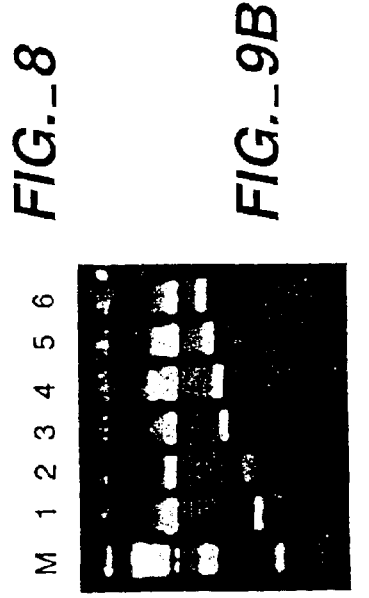
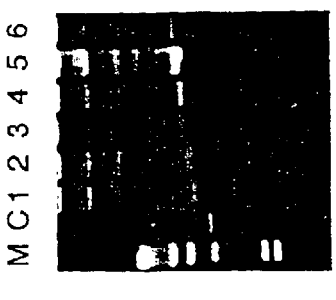
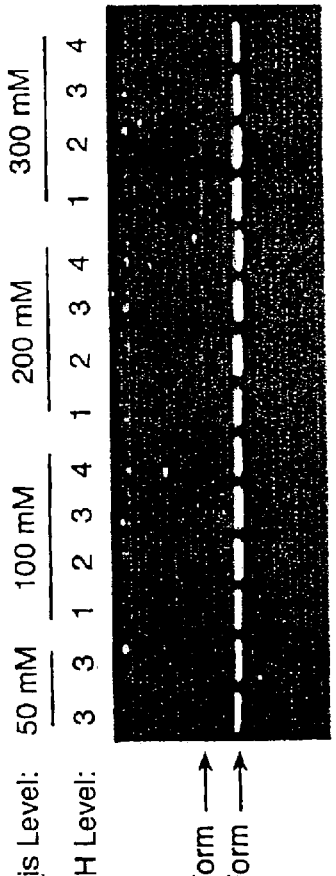
FIG._8
FIG._9B
FIG._9A
FIG._10

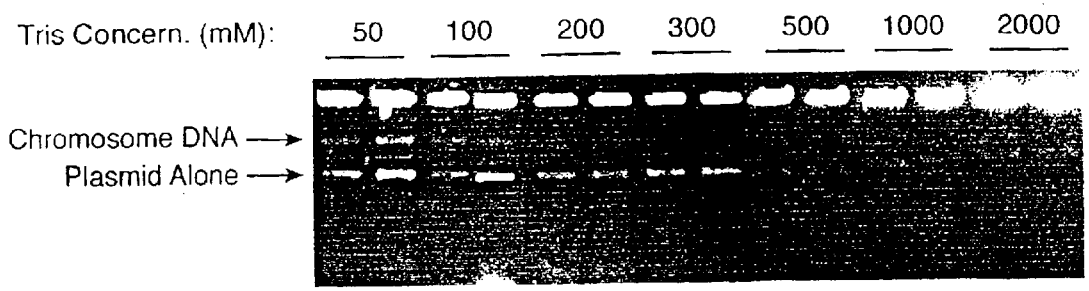
FIG._11
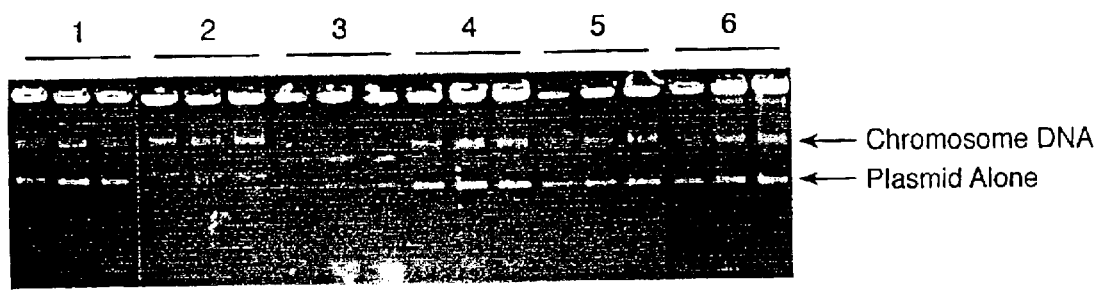
FIG._12
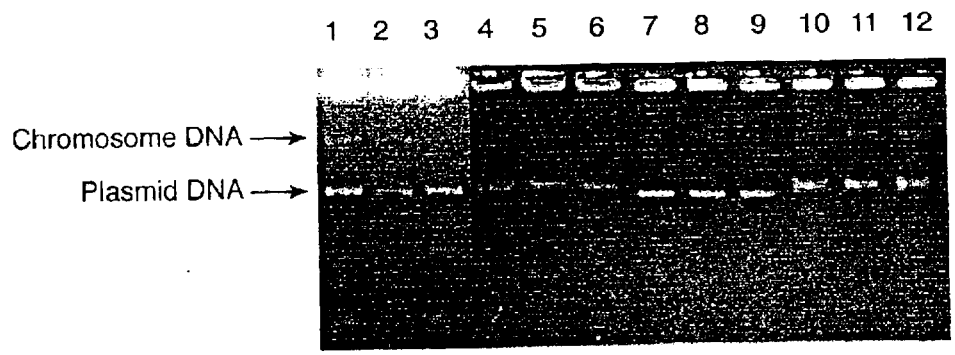
FIG._13

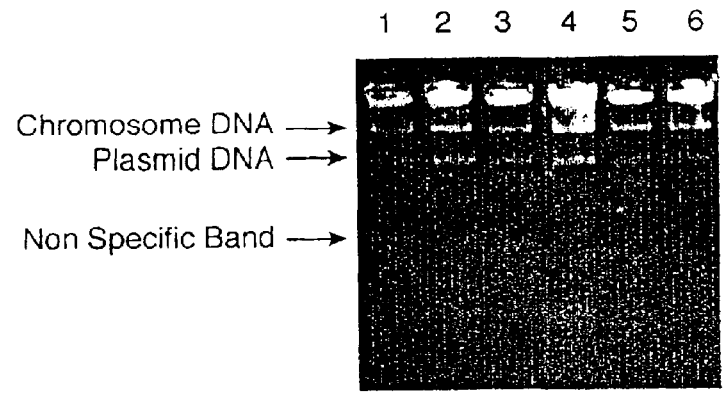
FIG._14
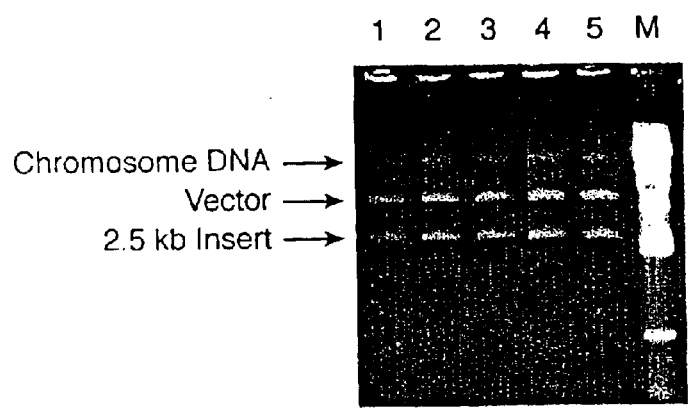
FIG._15
FIG._16
FIG._17

COMPOSITIONS AND METHODS FOR DIRECTLY AND RAPIDLY ANALYZING THE BIOCHEMICAL COMPONENTS OF MICROORGANISMS

This is a continuation of application Ser. No. 09/221,762, filed Dec. 28, 1998, now U.S. Pat. No. 6,265,164 which claims priority to provisional application Serial No. 60/079,506, filed Mar. 26, 1998, each of which is incorporated herein in its entirety.

FIELD OF THE INVENTION

The invention is directed to novel compositions and methods for the rapid and direct analysis of biochemicals from microorganisms. The compositions and methods of the present invention obviate the need for extracting and purifying the biochemicals prior to analysis.

BACKGROUND OF THE INVENTION

Microorganisms have long been studied and characterized by analysis of their biochemical constituents. Prior to analysis, the biochemical(s) of interest, such as DNA, RNA, lipids, proteins, carbohydrates or inorganic molecules, are often extracted and purified. However, extraction and purification procedures are time-consuming, labor-intensive, and are often the rate-limiting step, especially when multiple samples are being processed. Extraction and purification procedures also are expensive and often produce excessive amounts of material in comparison to the amounts required for analysis. Furthermore, these procedures often utilize hazardous chemicals and produce toxic waste that requires the implementation of expensive handling and disposal procedures.

As an example, bacteria harboring a plasmid with a cloned insert are commonly screened and identified by miniprep analysis (Ausubel et al. (1989) *Current Protocols in Molecular Biology*, Vol. 2, John Wiley & Sons, New York). This procedure requires culturing individual, transformed bacteria overnight in liquid media. The following day, plasmid DNA is extracted and purified from an aliquot of the overnight culture. Miniprep analysis involves multiple centrifugation steps, phenol and chloroform extractions, and precipitation steps. Once purified, the plasmid DNA is in most instances analyzed by gel electrophoresis. Often the plasmid DNA is restriction enzyme digested prior to electrophoresis to facilitate the identification of plasmids containing the appropriate insert. The miniprep procedure is time-consuming, requiring at least two days, utilizes toxic organic chemicals, such as phenol and chloroform, and is labor-intensive. In addition, only about 10% of the purified plasmid DNA is required for analysis.

Recently, a miniprep procedure has been reported that uses a modified alkaline lysis of the transformed bacteria to release the plasmid DNA with analysis of the supercoiled plasmid at the midway point of the purification procedure. Although this method is a modest improvement, its disadvantages again include the preparation of an overnight culture, plasmid extraction and purification, and restriction enzyme analysis to confirm the results (Biao et al., *BioTechniques* 23:601–607 (1997)).

Another approach to screening and identifying recombinant bacteria employs the polymerase chain reaction (PCR) (Costa and Weinter, *Strategies* 7:35–37 (1994)). This procedure does not require culturing the bacteria overnight in liquid media. The plasmid DNA is bacterial colonies from transformation plates is directly analyzed by PCR using primers that flank and amplify the insert, if present. Plasmids containing the cloned insert yield a PCR product of the appropriate size. Although this procedure appears to be convenient and rapid, it has the disadvantage that the PCR conditions and primer sets for each plasmid must be optimized before it can be used routinely. Additionally, synthesis and testing of primer pairs and PCR conditions is expensive and time-consuming. Moreover, when screening large inserts, PCR products are not as reliably produced. Under these circumstances, background amplification and the production of spurious PCR fragments may be problematic.

Large numbers of recombinant bacterial colonies can also be screened using other methods, such as colony hybridization and autoradiography (Sambrook et al. (1989) *Molecular Cloning: A Laboratory Manual*, 2nd ed. CSH Laboratory Press. Cold Spring Harbor, N.Y. ). However, this procedure is no longer routinely performed because many investigators prefer to avoid radioisotopes for safety, environmental, and financial reasons.

Much like the techniques for analyzing DNA molecules described above, techniques for analyzing RNA, protein or other non-nucleic acid components from microorganisms are also quite labor intensive and require elaborate extraction and/or purification steps prior to analysis of the component of interest.

Therefore, there is a significant interest in the development of novel methods for rapidly analyzing the biochemical components of microorganisms, wherein those method may be performed rapidly and directly without extraction and purification of the component of interest prior to analysis. There is also an interest in the development of novel methods for the analysis of biochemical components of microorganisms without the use of toxic or unsafe materials.

The present invention is based upon the fact that a single colony of a microorganism of interest has enough of a biochemical molecule of interest, such as DNA, RNA or protein, to detect using techniques available in the art, such as gel electrophoresis. As such, procedures and solutions have been developed such that these molecules may be detected and analyzed directly from the microorganism itself and without the need for prior extraction or purification of the molecule from other contaminating cellular components. These novel methods greatly enhance the ability to quickly and unambiguously detect and analyze cellular components of interest over those techniques that are currently available.

SUMMARY OF THE INVENTION

The present invention is directed to novel compositions and methods for analyzing biochemical components of microorganisms in a rapid and direct manner. The presently described compositions and methods allow for the analysis of a biochemical component of interest from a microorganism without prior extraction and/or purification of that component prior to analysis. In this way, biochemical components of a microorganism may be analyzed in a high throughput manner which provides unambiguous results.

One embodiment of the present invention is directed to a method for detecting the presence of a nucleic acid molecule in a microorganism without prior separation of that nucleic acid molecule from other cellular components, wherein the method comprises:

(a) suspending the microorganism in a first solution comprising from about 0.1% (v/v) to about 5% (v/v) of a nonionic detergent, wherein the detergent causes the lysis of the microorganism and the liberation of the nucleic acid molecule from the microorganism so as to provide a first suspension;

(b) optionally heating the first suspension for at least about 10 seconds at at least about 65° C.;

(c) combining the first suspension with a second solution comprising a restriction endonuclease so as to provide a second suspension, wherein the nucleic acid molecule is digested by the restriction endonuclease; and (d) detecting the presence of the nucleic acid molecule in the second suspension.

An additional embodiment of the present invention is directed to a method for detecting the presence of a nucleic acid molecule in a microorganism without prior separation of that nucleic acid molecule from other cellular components, wherein the method comprises:

(a) suspending the microorganism in a solution comprising (i) from about 0.1% (v/v) to about 5% (v/v) of a nonionic detergent and (ii) a restriction endonuclease, wherein the detergent causes the lysis of the microorganism and the liberation of the nucleic acid molecule from the microorganism and wherein the restriction endonuclease digests the liberated nucleic acid molecule, the step of suspending providing a suspension; and (b) detecting the presence of the nucleic acid molecule in the suspension.

Yet another embodiment of the present invention is directed to a method for detecting the presence of a biochemical component in a microorganism without prior separation of that biochemical component from other cellular constituents, wherein the method comprises:

(a) suspending the microorganism in a first solution comprising a component that substantially prevents DNase activity so as to provide a first suspension;

(b) combining the first suspension with a second solution comprising an alkaline buffer and a detergent so as to provide a second suspension, wherein the biochemical component is liberated from the microorganism; and (c) detecting the presence of the biochemical component in the second suspension.

Additional embodiments of the present invention are directed to kits that comprise one or more of the solutions employed in the above described methods.

Additional embodiments will be evident to those skilled in the art upon a reading of the present disclosure.

BRIEF DESCRIPTION OF THE DRAWINGS

FIG. 1. Release of DNA from bacteria by restriction enzyme digestion. Colonies of pcDNA3 transformants were picked directly from an overnight-cultured transformation plate, suspended in 0.5% Triton X-100, 10 mM Tris-HCl (pH 8.0) and treated with the following restriction enzymes: EcoRI (1), SacII (3) and inactive SacII (4). Two (2) is a negative control (no restriction enzyme treatment). Lambda DNA/HindIII molecular weight markers are shown in Lane M.

FIGS. 2A–D. Release and analysis of transformants containing plasmids with inserts of 0.28 kbp (FIG. 2A); 0.68 kbp (FIG. 2B); 0.9 kbp (FIG. 2C) and 2.5 kbp (FIG. 2D). The left lane in each panel is λ/HindIII molecular weight markers.

FIG. 3. Effects of different detergents on release of plasmid DNA from bacteria by restriction enzyme digestion. Recombinant colonies were picked from transformation plates that had been incubated over night and suspended in 10 mM Tris-HCl (pH 8.0) and either of 0.5% Triton X-100, 0.5% SDS, 0.2% Tween-20 or 0.5% NP40 and digested with NheI/XhoI. Lambda DNA HindIII molecular weight markers are shown in Lane M.

FIG. 4. NheI/XhoI digest of Clone A transformants treated with the following: Lanes 1–3: $H_2O$; Lanes 4–6: 10 mM Tris-HCl (pH 8.0); Lanes 7–9: 0.1% Triton X-100 and 10 mM Tris-HCl (pH 8.0); Lanes 10–12: 0.5% Triton X-100 and 10 mM Tris-HCl (pH 8.0); Lanes 13–15: 1.0% Triton X-100 and 10 mM Tris-HCl (pH 8.0); Lanes 16–18: 2.5% Triton X-100 and 10 mM Tris-HCl (pH 8.0); Lanes 19–21: 5.0% Triton X-100 and 10 mM Tris-HCl (pH 8.0).

FIG. 5. Effects of heating on the release of plasmid DNA by restriction enzyme digestion. Recombinant colonies were picked directly from transformation plates that had been incubated overnight, suspended in 0.5% Triton X-100, 10 mM Tris-HCl, (pH 8.0), incubated at 100° C. for the indicated periods of time, NheI/XhoI digested, and electrophoresed. Lambda DNA HindIII molecular weight markers are shown in Lane M.

FIG. 6. Effects of heating on the release of plasmid DNA by restriction enzyme digestion. Recombinant colonies were picked directly from transformation plates that had been incubated overnight, suspended in 0.5% Triton X-100, 10 mM Tris-HCl, (pH 8.0), incubated at 65° C. for the indicated periods of time, NheI/XhoI digested, and electrophoresed. Lambda DNA HindIII molecular weight markers are shown in Lane M.

FIG. 7. Effects of microwave treatment on the release of plasmid DNA by restriction enzyme digestion. Recombinant colonies were picked directly from transformation plates that had been incubated overnight, suspended in 0.5% Triton X-100, 10 mM Tris-HCl, (pH 8.0), microwaved for the indicated periods of time, NheI/XhoI digested, and electrophoresed. Lambda DNA HindIII molecular weight markers are shown in Lane M.

FIG. 8. Analysis of DNA released by the chemical method. Seven recombinant plasmids with 2.5 kbp inserts were identified in Lanes 3, 4, 5, 9, 14, 16, and 18. Lane S contains supercoiled DNA markers (2.9, 3.9, 5.4, and 10 kbp). Lambda DNA HindIII molecular weight markers are shown in Lane M.

FIGS. 9A–B. Agarose gel analysis of six recombinant plasmids (Lanes 1–6) released by the chemical method (Panel A) and miniprep/restriction enzyme method (Panel B). Lane C, Panel A shows the undigested 5.4 kbp vector without an insert. Lambda DNA HindIII molecular weight markers are shown in Lane M.

FIG. 10. Effect of Tris and NaOH concentrations and ratios on the configuration of plasmid DNA released by the chemical method. 20 ng of plasmid DNA was treated with the indicated concentrations of Tris-HCl, (pH 8.0) and the following concentrations of NaOH (0.2% NaOH (Level 1); 0.4% NaOH (Level 2); 0.8% NaOH (Level 3); 1.6% NaOH (Level 4).

FIG. 11. Effect of Tris-HCl concentration on the release of DNA by the chemical method. Individual colonies from transformation plates were suspended in Disperse Solution containing the indicated concentrations of Tris-HCl (pH 8.0), treated with 0.8% NaOH, 1% SDS, and electrophoresed in agarose gels.

FIG. 12. Comparison of DNA released using different sets of Disperse and Denature Solutions: (1) 50 mM Tris-HCl (pH 8.0), 10 mM EDTA and 0.8% NaOH, 1% SDS; (2) 50 mM Tris-HCl (pH 8.0), 10 mM EDTA and 0.8% NaOH; (3) 50 mM Tris-HCl (pH 8.0), 10 mM EDTA and 1% SDS, (4) 50 mM Tris-HCl (pH 8.0) and 0.8% NaOH, 1% SDS; (5) 10 mM EDTA and 0.8% NaOH 1% SDS; (6) 0.5% Triton X-100 and 0.8% NaOH, 1% SDS.

FIG. 13. Effects of different detergents on DNA released by the chemical method. Lanes 1–3: Disperse Solution (50 mM Tris-HCl (pH 8.0), 10 mM EDTA and Denature Solution (0.8% NaOH, 1% SDS). Lanes 4–6: Disperse Solution (50 mM Tris-HCl (pH 8.0), 10 mM EDTA and Denature Solution (0.2% Triton X-100, 0.8% NaOH, 1% SDS). Lanes 7–9: Disperse Solution (50 mM Tris-HCl (pH 8.0), 10 mM EDTA and Denature Solution (0.2% Tween-20, 0.8% NaOH, 1% SDS). Lanes 10–12: Disperse Solution (50 mM Tris-HCl (pH 8.0), 10 mM EDTA and Denature Solution (0.2% NP40, 0.8% NaOH, 1% SDS).

FIG. 14. Comparison of SDS and sarcosine DNA release by the chemical method. Lanes 1–3: Denature Solution (0.8% NaOH, 1% SDS). Lanes 4–6: Denature Solution (0.8% NaOH, 1% Sarcosine).

FIG. 15. Plasmid DNA release from bacterial glycerol stocks by restriction enzyme method. Lanes 1–5 are Clone A DNA with 2.5 kbp inserts directly released by the restriction enzyme method using NheI/XhoI from 0.5, 1.0, 1.5, 2.0 and 2.5 µl, respectively, of a bacterial glycerol stock.

FIG. 16. 1% Agarose gel analysis of RNA released directly from a single bacteria using the chemical method. Disperse Solution: 300 mM Tris-HCl, pH 8.0. Denature Solution: 0.4% NaOH, 1% SDS.

FIG. 17. Analysis of bacterial genomic DNA released by restriction enzyme method. Individual colonies of DH10B bacteria were suspended in 0.5% Triton X-100, 10 mM Tris-HCl (pH 8.0) and digested with EcoRI for 16 hours at 37° C.

DETAILED DESCRIPTION OF THE INVENTION

The present invention is directed to novel compositions and methods for analyzing biochemical components of microorganisms in a rapid and direct manner. The presently described compositions and methods allow for the analysis of a biochemical component of interest from a microorganism without prior extraction and/or purification of that component prior to analysis. In this way, biochemical components of a microorganism may be analyzed in a high throughput manner which provides unambiguous results.

In one embodiment of the present invention referred to herein as the restriction endonuclease method, one may detect the presence of a nucleic acid molecule in a microorganism without prior separation of that nucleic acid molecule from other cellular components. One important finding that led to this method was that restriction endonuclease digestion was important for releasing, separating and separately visualizing a DNA insert, plasmid DNA and genomic DNA directly from a microorganism. In this regard, "microorganisms" that find use in the presently described methods include, for example, bacterial cells, yeast cells, eukaryotic cells and viruses, including bacteriophage, and the like. The nucleic acid molecule being detected is preferably an extrachromosomal or genomic DNA molecule, wherein the DNA molecule can be single-stranded or double-stranded depending on the microorganism from which the DNA molecule originates. By "extrachromosomal DNA molecule" herein is meant an episome, such as a plasmid, or a vector that can be linear or circular and which is not incorporated into the genome of the microorganism. Exogenous nucleic acid that is incorporated into the genome of the microorganism is encompassed within the definition of genomic DNA.

The microorganisms that find use in the present invention may be obtained in a variety of ways known in the art. Preferably, the microorganism is a bacterium which may be transformed with an exogenous nucleic acid molecule and is obtained as an isolated colony on solid media or from a liquid culture. Yeast organisms that find use herein may be obtained in a variety of ways known in the art including, for example, from a single colony obtained from a solid growth medium culture. Eukaryotic cells and viruses that find use herein may be obtained by methods conventionally employed in the art including, for example, from tissue culture, and the like.

In one embodiment of the restriction endonuclease method, once obtained, the microorganism is suspended in a first solution that optionally comprises an ionic or non-ionic detergent at a concentration that does not significantly affect the function of a subsequently added restriction endonuclease, wherein that concentration may be determined empirically. The first solution is chosen so as to provide a certain degree of lysis of the microorganism and may constitute water. Preferably, the first solution comprises from about 0.1% (v/v) to 5% (v/v), preferably from 0.1% (v/v) to 2.5% (v/v), more preferably from 0.25% (v/v) to 1.5% (v/v), and most preferably about 0.5% (v/v) of a nonionic detergent which functions to disrupt or compromise the outer cell wall or membrane, thereby causing lysis of the microorganism and liberation of the intracellular components of the microorganism, including the nucleic acid molecule of interest. Nonionic detergents that find use in the present invention include, for example, Triton X-100, Tween-20, NP-40, commercially obtained dishwashing detergents, and the like, preferably Triton X-100, and will be chosen and employed such that they will not substantially inhibit the activity of a subsequently added restriction endonuclease, but will help restriction enzymes to access the target DNA.

In addition to the other components of the first solution such as a nonionic detergent, the "first solution" may also optionally comprise any of a number of well known and routinely employed buffers, preferably Tris-HCl, pH 8.0 or STET, as well as any of a number of other components that will not substantially affect the activity of a subsequently added restriction endonuclease. Such additional components include, for example, RNase, lysozyme, and the like. In a preferred embodiment, the first solution does not comprise SDS or EDTA or any other component that will substantially affect the activity of a subsequently added restriction endonuclease.

Suspending the microorganism in the above described first solution will cause lysis of the microorganism and liberation of the intracellular components of the microorganism, including the nucleic acid molecule of interest, thereby providing a first suspension of components that comprises the nucleic acid molecule of interest. The presence of endogenous microorganism-derived DNAses in the first suspension may act to destroy plasmid or genomic DNA prior to analysis of the nucleic acid molecule. To minimize or prevent this non-specific DNA degradation, the first suspension may be optionally heated to inactive endogenous DNAses before restriction enzyme digestion. Short periods of heating should be avoided because they may activate endogenous DNAses. In addition, long heating period or heating at excessive temperatures may denature the double-stranded DNA to a single-stranded form, which is not susceptible to restriction endonuclease digestion and, therefore, will not be released.

In light of the above, the first suspension may optionally be heated to at least about 65° C. for at least about 10 seconds, preferably at least about 30 seconds, in order to inactivate the endogenous DNase activity. In other embodiments, the first suspension may optionally be heated at about 100° C. for at least about 10 seconds, preferably about 1 minute so as to destroy endogenous DNase activity. The time and temperature of this optional heating step may be determined by the skilled artisan in a routine manner.

The first suspension obtained from suspending the microorganism in the above described first solution may then be directly, and without extraction or purification of the nucleic acid molecule of interest from any other cellular component, combined with a second solution that comprises a restriction endonuclease, thereby providing a second suspension. The buffer conditions of the second suspension will be chosen such that the restriction endonuclease will be capable of digesting the nucleic acid molecule of interest, wherein the buffer conditions will vary depending upon the nature of the restriction endonuclease and the manufacturer's instructions for optimal buffer conditions. Preferably, no component present in the second suspension will substantially inhibit the endonuclease's ability to digest the nucleic acid molecule of interest. The second suspension may be incubated for varying times and temperatures so as to achieve either partial or substantially complete digestion of the nucleic acid molecule as desired. In regard to the above, it has been herein discovered that restriction endonuclease digestion is required for allowing gel separation of the liberated nucleic acid components of the microorganism.

In preferred embodiment of the restriction endonuclease method, Type II restriction endonucleases such as, EcoRI, NheI, XhoI, NotI, BamHI, HindIII, are employed because they recognize specific nucleotide sequences and their activity can be easily monitored and regulated (see New England Biolabs Catalog, which is expressly incorporated by reference in its entirely). In alternative embodiments, however, other types of endonucleases may be employed.

Once the restriction endonuclease has been allowed to digest the nucleic acid molecule as desired, the presence of the nucleic acid molecule may be detected in a variety of ways which are well known in the art. Such means of detection include, for example, gel electrophoresis, Southern blot analysis, Northern blot analysis, polymerase chain reaction analysis, chromatography, and the like. Such techniques are well known in the art and may be routinely employed for such detection. Often, when the restriction endonuclease method is employed to detect the presence of a cloned insert in a vector, the method employed for detecting the presence of the nucleic acid will be capable of determining the approximate size of the detected nucleic acid.

In another embodiment of the restriction endonuclease method, the microorganism of interest may be suspending in a single solution that comprises from about 0.1% (v/v) to 5% (v/v), preferably from 0.1% (v/v) to 2.5% (v/V), more preferably from 0.25% (v/v) to 1.5% (v/v), and most preferably about 0.5% (v/v) of a nonionic detergent and a restriction endonuclease that functions to digest the nucleic acid molecule liberated by treatment of the microorganism with the detergent. The digested nucleic acid molecule may then be analyzed as described above. An especially preferred embodiment employs a first solution that comprises 0.5% Triton X-100, 10 mM Tris-HCl and 1 mM EDTA.

In yet another embodiment of the present invention designated herein as the chemical method, a biochemical component of a microorganism may be detected without prior separation of that component from other cellular constituents of the microorganism. By "biochemical component", herein is meant a nucleic acid, such as DNA and RNA, or analogs thereof, a protein, a lipid, a carbohydrate, and the like. By "DNA" herein is contemplated a genome of a microorganism or an extrachromosomal DNA and can be single-stranded or double-stranded depending on the microorganism from which the DNA originates. By "extrachromosomal DNA" herein is meant an episome, such as a plasmid, or a vector that can be linear or circular. By "RNA" herein is contemplated a genome of a microorganism, an extrachromosomal element, a vector, a transfer RNA, a messenger RNA, a nuclear RNA, or a ribosomal RNA. Depending on the microorganism from which the RNA originates and the type of RNA, it too can be single-stranded or double-stranded. By "analogs thereof" herein is contemplated nucleic acids, whether single-stranded or double-stranded, containing one or more non-natural or synthetic bases or a modified backbone, such as peptide nucleic acids (PNAs), nucleic acids comprising one or more internucleotide atoms such as sulfur, oxygen, nitrogen, and the like.

With specific regard to the above, it has been discovered that gel electrophoresis of plasmid DNA under certain specified alkaline conditions is important for obtaining an informational resolution of a single sharp band of supercoiled plasmid DNA. In one embodiment of the invention, a microorganism of interest may be suspended in a first solution that comprises a component that is capable of substantially preventing DNase activity, wherein such components include all known DNase inhibitors, preferably EDTA. In preferred embodiments, the component that is capable of substantially preventing DNase activity is EDTA which may be present from about 0.1 mM to about 100 mM, preferably from about 0.1 mM to about 50 mM, more preferably from about 0.2 mM to about 25 mM and most preferably about 10 mM EDTA. The first solution may also comprise virtually any type of buffer solution, provided that that buffer solution does not substantially interfere with the ability to liberate a biochemical component of interest from the microorganism or to detect that biochemical component. A preferred buffer comprises Tris-HCl, which in certain embodiments may be present from about 1 mM to about 300 mM.

The first solution employed in the chemical method may also comprise a detergent which may be a detergent selected from the group consisting of Triton X-100, Tween-20, NP40, a sarcosine-based detergent, SDS, and the like. For the most part, the detergent will be present in the first solution at a concentration from about 0.1% (v/v) to about 10% (v/v), preferably from about 0.1% (v/v) to about 5% (v/v), more preferably from about 0.1% (v/v) to about 2.5% (v/v), most preferably at about 0.5% (v/v). In a particularly preferred embodiment, the first solution comprises about 50 mM Tris-HCl (pH 8.0), about 10 mM EDTA, about 0.5% (v/v) Triton X-100 and about 100 µg/ml RNase A.

Subsequent to suspending the microorganism in the above described first solution so as to provide a first suspension, the first suspension may be combined with a second solution which comprises (i) an alkaline buffer and (ii) a detergent, so as to provide a second suspension. The alkaline buffer may comprise any buffer having a pH greater than 7.0, usually greater than 8.0, more usually greater than 9.0, preferably greater than 10.0, more preferably greater than 11.0 and most preferably greater than 12.0, providing that that buffer does not substantially interfere with the ability to detect the presence of the biochemical component of interest in the second suspension. Preferred alkaline buffers include, for example, hydroxyl group-containing buffers which may be, for example, NaOH, KOH, CaOH, and the like, preferably NaOH. For the most part, the alkaline buffer will be present at a concentration of about 0.2% to 1.6%, although concentrations outside of these ranges may also find use herein.

The second solution employed in the chemical method also comprises a detergent which may be a detergent selected from the group consisting of Triton X-100, Tween-20, NP40, a sarcosine-based detergent, SDS, and the like. For the most part, the detergent will be present in the second solution at a concentration from about 0.1% (v/v) to about 10% (v/v), preferably from about 0.1% (v/v) to about 5% (v/v), more preferably from about 0.1% (v/v) to about 2.5% (v/v), most preferably at about 0.5% (v/v). A particularly preferred second solution comprises about 0.8% (v/v) NaOH, 0.5% (v/v) SDS, 0.5% N-lauroylsarcosine and 0.2% (v/v) Tween-20. All of the above described solutions may optionally include molecular weight indicator dyes for agarose gel electrophoresis.

In a particularly preferred embodiment of the herein described chemical method, the microorganism of interest may be suspended in a single solution that is a composite of the above described first and second solutions, followed by analysis of the biochemical component of interest. Analysis of the liberated biochemical component of interest may occur by any of a number of well known techniques for detecting the presence of a biochemical component of interest and as described above.

With regard to both the restriction endonuclease embodiments and chemical method embodiments described above, the following pointers may optionally be followed.

(1) Apply to any format of bacteria—colonies, fresh culture and glycerol stock. The methods and kits can be used for screening of any format of bacteria containing a plasmid: plate colonies, fresh culture and glycerol stock. Usually, plate colonies produce stronger plasmid DNA bands and liquid culture has less background for gel analysis.

(2) Grow Bacteria for more than 20 hours. One may optionally transform in morning of first day and doing screening work in next day, so there will be more than 20 hours for bacteria growing. Large and well-grown colonies are always easily analyzed. To get well-isolated and well-grown colonies, one may wish to spread less than 300 colonies per 90-mm medium plate.

(3) Check bacterial clones in liquid culture. Both larger scale method and enzyme digestion method can check bacterial clones in over night cultured liquid medium or glycerol stock culture. Simply take 1 to 3 $\mu$l of liquid culture of bacterial clones as the starting material to perform the screening procedure. When using poorly grown bacteria, the starting bacterial volume may increase to 5 $\mu$l and the reaction volume increased to 15 to 20 $\mu$l in the restriction digest method. If necessary, one can use more of the bacteria culture, but it is recommend that the bacterial culture is spun down prior to screening.

(4) Use freshly prepared agar medium plates. One may wish to use freshly prepared agar medium plates to culture bacterial colonies for screening.

(5) Bacterial colony growing for 1 to 2 days may give the best results. Bacterial colonies in medium plates will become dry and hard after being stored or cultured for several days at room temperature or 4° C. One may not wish to use more than 3-day old colonies for enzyme digest screening and 7-day old colonies for the chemical screening method.

(6) Set up master plates to transfer colonies.

(7) Use appropriate amount of restriction enzyme in digest: Usually 0.5 unit of restriction enzyme is needed in each digest reaction. Incubation period of time is dependent on the amount of digest enzymes. One unit per reaction often requires 20 to 30 minutes per incubation, while 1 $\mu$l of restriction enzyme (10 to 20 units) often needs only 5 minutes incubation.

(8) Perform a double restriction enzyme digest. When two different buffers have to be used for double enzymes digest, one may wish to use the first buffer with lower salt concentration to perform the first digest in 10 $\mu$l volume of reaction for 10 min and then simply add the second buffer and enzyme for second digest by scaling up to 15 or 20 $\mu$l reaction volume.

(9) Load samples before submerging gel in running buffer. One may wish to load samples directly into the loading wells of the agarose gel before submerging the gel in running buffer, otherwise the samples may be lost.

(10) Use freshly prepared agarose gel. It is recommended to use freshly prepared gel (within 30 minutes after pouring off). Because sample loading is performed before submerging gel in running buffer, loading wells of gel, if over-dried, will absorb and separate the samples into two sides of wells and generate diffused bands eventually.

(11) Post-stain agarose gel—no ethidium bromide in gel or running buffer. One may wish to use post-staining of gel with ethidium bromide (EB).

(12) Use fresh prepared EB staining buffer. Fresh staining buffer may be made from EB stock solution (10 mg/ml). Old used staining EB buffer, like more than one day after the first use will increase background significantly and results in difficulty in observing target DNA bands.

(13) Use low EB concentration for staining: high concentration of EB for staining may quickly increase background and result in difficulty in recognizing target bands. One may wish to use less than 0.5 (g/ml EB staining solution for post staining of gel for a little longer staining (more than 10 minutes).

(14) Refer supercoiled marker to monitor and interpret DNA bands on gel. The mobility of supercoiled vector DNA on agarose gel is different from that of linearized DNA.

(15) Take picture to analyze results. Sometimes target DNA bands may not be visible directly on an agarose gel because of less copy number of plasmid in bacteria. One may wish to take a photograph of a gel for analysis and documentation of screening results by using high aperture (4.5) and long exposure (about 2–5 seconds).

(16) Fastest bands are targets on gel. There may be four bands observable for each colony if picking up large piece of colonies and gel running time long enough on gel in large scale screening method. The fastest moving bands are strong and informative. So comparison may often be made between the first bands of colonies and that of control markers. Sometimes non-nucleic acid material and degraded RNA will show up like diffuse bands on the bottom on gel. In that case, one may wish to always refer to the movement of supercoiled marker bands or linearized marker DNA and locate the target bands. In addition, it is better to load the vector DNA without insert as exact control if that is available.

(17) Increase DNA band signal—incubation of well-grown bacteria. Freshly cultured and large bacterial colonies can produce strong DNA bands for easy identification of recombinants.

Additional embodiments of the present invention are directed to kits that comprise one or more of the above described solutions for use in the herein described methods.

Further details of the invention are illustrated in the following non-limiting examples.

EXPERIMENTAL

Example 1

Release and Analysis of Plasmid DNA by Restriction Enzyme Digestion and Agarose Gel Electrophoresis E. coli strain Top10F' was transformed with a vector designated pcDNA3.1 (Invitrogen) having insert sizes of 0.28 kbp, 0.68 kbp, 0.9 kbp or 2.5 kbp and cultured overnight on LB agar plates containing ampicillin. The following day, approximately 25–50% of isolated colonies measuring about 1–2 mm in diameter were aseptically picked from the transformation plates and placed in 8 µl of 0.5% Triton X-100 and 10 mM Tris-HCl (pH 8.0). Each sample then received 2 µl of restriction enzyme mixture (1 µl 10×restriction enzyme buffer and 1 µl restriction endonuclease; either EcoRI, SacII, or inactive SacII; 0.5 U per reaction) and was incubated at 37° C. for 30 minutes. For agarose gel electrophoresis, the samples were loaded onto 0.8% to 1.2% agarose gels and electrophoresed in 1×TAE or 1×TBE running buffer. The gel was then stained in 0.5 µg/ml ethidium bromide and the DNA was visualized by ultraviolet transillumination.

The results shown in FIG. 1 indicate that chromosomal and plasmid DNA were released and detected following digestion with EcoRI and SacII. DNA was not detected in samples that did not receive enzyme or received inactive enzyme. Thus, digestion by the enzyme appears to play a key role in the release of DNA from the bacterial cell and the ability to subsequently visualize that DNA.

In addition, bacterial transformants containing plasmids with inserts ranging from 0.28 kbp to 2.5 kbp were treated as described above but where the following restriction endonucleases were employed to digest and release the DNA; FIG. 2A—NheI/HindIII, FIG. 2B—NheI/BamHI, FIG. 2C—NotI/BamHI and FIG. 2D—NheI/XhoI. As shown in FIGS. 2A–D, the inserts from each plasmid were efficiently released and identified, demonstrating that inserts of varying sizes could be identified using this method.

Example 2

Detergent and DNA Release and Analysis by Restriction Enzyme Digestion and Agarose Gel Electrophoresis In the following experiment, 10 mM Tris HCl (pH 8.0) containing either 0.5% Triton X-100, 0.5% SDS, 0.2% Tween-20, or 0.5% NP40 were compared. E. coli strain DH10B was transformed with Clone A (a 5.4 kbp plasmid with a 2.5 kbp insert flanked by NheI and XhoI sites) and cultured overnight on LB agar plates containing ampicillin. The following day, approximately 25–50% of three, isolated colonies measuring about 1–2 mm in diameter were aseptically picked from the transformation plates, suspended in 8 µl of 10 mM Tris-HCl (pH 8.0) and either 0.5% Triton-100, 0.5% SDS, 0.2% Tween-20, or 0.5% NP40. Each sample received 2 µl of restriction enzyme mix (1 µl 10×RE buffer and 1 µl restriction endonuclease) and was incubated at 37° C. for 30 minutes. For agarose gel electrophoresis, the samples were loaded onto 0.8% to 1.2% agarose gels and electrophoresed in 1×TAE or 1×TBE running buffer. The gel was then stained in 0.5 µg/ml ethidium bromide and the DNA was visualized by ultraviolet transillumination.

The results shown in FIG. 3 indicate that Clone A was digested and released its 2.5 kbp insert using 10 mM Tris-HCl (pH 8.0) containing Triton X-100, Tween-20 and NP40. In contrast, no insert was detected in samples treated with SDS, which most likely, inhibits or inactivates the restriction enzymes.

Further studies demonstrated that the Triton X-100 concentration in the 10 mM Tris-HCl (pH 8.0) solution can vary from about 0.1% to about 5.0%, with 0.5% Triton X-100 being the optimum concentration. Clone A transformants were dispersed in each of the following solutions: (1) $H_2O$, (2) 10 mM Tris-HCl (pH 8.0), (3) 0.1% Triton X-100 and 10 mM Tris-HCl (pH 8.0), (4) 0.5% Triton X-100 and 10 mM Tris-HCl (pH 8.0), (5) 1.0% Triton X-100 and 10 mM Tris-HCl (pH 8.0), (6) 2.5% Triton X-100 and 10 mM Tris-HCl (pH 8.0), or (7) 5.0% Triton X-100 and 10 mM Tris-HCl (pH 8.0) and NheI/XhoI digested. As shown in FIG. 4, DNA was efficiently released and digested using 10 mM Tris-HCl (pH 8.0) and Triton X-100 concentrations ranging from 0.1% to 5.0%, with 0.5% yielding the best results.

Example 3

The Affects of Temperature on DNA Release and Analysis by Restriction Enzyme Digestion Because bacteria contain endogenous nucleases, such as DNAses, that may digest plasmid DNA, we examined the affect of heat inactivation of these enzymes on release of plasmid DNA by restriction enzyme digestion.

Clone A transformants were picked from agar plates and dispersed in 0.5% Triton X-100, 10 mM Tris-HCl (pH 8.0)as described in Example 1 and incubated at either 100° C. for from 10–180 seconds or 65° C. for 1–10 minutes prior to NheI/XhoI digestion (see Example 2). As shown in FIG. 5, incubation at 100° C. for 10–60 seconds increased the yield of plasmid DNA in comparison to unheated samples. However, plasmid yields decreased following incubation at 100° C. for 90 seconds and no DNA was observed in samples heated at 100° C. for 180 seconds. Similarly, incubating samples at 65° C. for 1,5, or 10 minutes prior to restriction enzyme digestion improved plasmid DNA yields in comparison to untreated samples, which, in this instance, showed evidence of plasmid DNA degradation (FIG. 6).

We also tested the affect of microwave treatment on endogenous nuclease inactivation and plasmid DNA release. Samples were dispersed as described above and incubated for 0.5–3.0 minutes in a microwave set at the highest setting. The results indicated that plasmid DNA was efficiently released and restriction enzyme digested following microwave treatment. In this instance, the DNA bands observed following agarose gel electrophoresis were diffuse when compared to samples incubated at 100° C. for 30 seconds (FIG. 7).

Example 4

Release and Analysis of DNA from Different Bacterial Strains Using Various Restriction Endonucleases This experiment demonstrates that plasmid DNA can be directly analyzed from different bacterial strains using a variety of restriction endonucleases. *E. coli* strains XL1 blue, DH5a, NM522, JM109, DH10B, and Top10F' were transformed with Clone A, plated onto LB agar medium containing ampicillin, and incubated overnight. Portions of isolated colonies were suspended in 8 μl of 0.5% Triton X-100, 10 mM Tris-HCl (pH 8.0). Samples were then individually digested by adding 2 μl of a solution containing either EcoRI, NheI, XhoI, XbaI, NotI, CaII, HindIII, BamHI, SacII, and BstEII and electrophoresed (see Example 1). The results indicated that there were no obvious differences between the strains in regards to plasmid DNA release by each of the restriction enzymes tested (data not shown).

Example 5

DNA Release and Analysis from Bacteria by Chemical Treatment

*E. coli* strain DH10B was transformed with Clone A or a 5.4 kbp plasmid (Clone A without its 2.5 kbp insert), plated onto LB agar plates and incubated overnight. Approximately 25–50% of 18 isolated colonies measuring about 1–2 mm in diameter were aseptically picked from the transformation plates and dispersed in 4 μl 50 mM Tris-HCl (pH 8.0), 10 mM EDTA (Disperse Solution). To each sample was added 4 μl of 0.8% NaOH, 1% SDS (Denature Solution). For agarose gel electrophoresis, the samples were loaded onto 0.8% to 1.2% agarose gels and electrophoresed in 1×TAE or 1×TBE running buffer. The gel was then stained in 0.5 μg/ml ethidium bromide and the DNA was visualized by ultraviolet transillumination.

The results shown in FIG. 8, identified seven colonies that contained Clone A based on the slower migration rate of their plasmids in agarose gels in comparison to the 5.4 kbp vector. To verify these results, six additional recombinants containing inserts ranging from 0.9–2.5 kbp were analyzed by the chemical and the classical miniprep/restriction enzyme digestion methods. As shown in FIG. 9A, the recombinant plasmids directly analyzed by the chemical method, described above, had a decreased mobility on agarose gels that was proportional to the size of their inserts. These results also agreed with the results obtain by the miniprep/restriction enzyme digestion method shown in FIG. 9B.

Plasmid DNA was analyzed from *E. coli* strains XL1 blue, DH5a, NM522, JM109, DH10B, and Top10F' using the chemical method, described above. For each strain, DNA was successfully released and analyzed. For those strains containing a lower plasmid copy number, the yield of released DNA was increased by using a larger number of bacteria (data not shown).

Example 6

The Affects of Tris and NaOH Concentration on Plasmid DNA Conformation and Migration in Agarose Gels To determine the affect of NaOH/Tris ratios employed in the Chemical Method described above (see Example 5) on plasmid DNA conformation and migration in agarose gels, 20 ng of plasmid DNA was placed in 4 μl Disperse Solution containing either 50 mM, 100 mM, 200 mM, or 300 mM Tris-HCl (pH 8.0) and 10 mM EDTA followed by addition of 4 μl of a Denature Solution containing either 0.2%, 0.4%, 0.8%, or 1.6% NaOH and 1% SDS. As shown in FIG. 10, the conformation of the plasmid DNA is dependent upon the relative concentrations of Tris-HCl and NaOH. Higher NaOH concentrations decreased the amount of the linear form of the plasmid while higher Tris concentrations increased the amount of the linear form. Linear plasmid was not observed at higher NaOH to Tris ratios which also produced very sharp bands of supercoiled plasmid DNA.

To determine the affect of Tris concentration on the release and mobility of DNA from bacteria, individual colonies of Clone A were aseptically taken from a transformation plate that had been incubated overnight and dispersed in 4 μl of either 50 mM, 100 mM, 200 mM, 300 mM, 500 mM, 1000 mM or 2000 mM Tris-HCl (pH 8.0), 10 mM EDTA followed by an 4 μl of 0.8% NaOH and 1% SDS. As shown in FIG. 11, 50–300 mM Tris-HCl (pH 8.0) resulted in maximum release of plasmid DNA. Tris-HCl concentrations from about 200–300 mM resulted in less background due to the decreased amount of chromosomal DNA that was released. Tris-HCl concentrations 500 mM and higher, significantly decreased the amount of plasmid and chromosomal DNA that was released and decreased their mobility on agarose gels.

Example 7

Analysis of Components for Release of Plasmid DNA by Chemical Treatment

The release of plasmid DNA from bacteria was analyzed using the following sets of Disperse and Denature Solutions, respectively: (1) 50 mM Tris-HCl (pH 8.0), 10 mM EDTA; 0.8% NaOH, 1% SDS; (2) 50 mM Tris-HCl (pH 8.0), 10 mM EDTA; 0.8% NaOH; (3) 50 mM Tris-HCl (pH 8.0), 10 mM EDTA; 1% SDS; (4) 50 mM Tris-HCl (pH 8.0); 0.8% NaOH, 1% SDS; (5) 10 mM EDTA; 0.8% NaOH, 1% SDS and (6) 0.5% Triton X-100.

Colonies of *E. coli* that had been transformed with Clone A were treated with the five Disperse and Denature Solution sets and analyzed by agarose gel electrophoresis. As shown in FIG. 12, plasmid DNA was released in each of the Disperse and Denature Solution sets. However, the use of 0.8% NaOH alone as the Denature Solution decreased DNA migration. In contrast, 1% SDS Denature Solution increased the mobility of chromosomal DNA and resulted in difficulty in differentiating it from plasmid DNA. The 50 mM Tris-HCl Dispersant Solution more efficiently released the bacterial DNA in comparison to 10 mM EDTA. Interestingly, Triton X-100, which can be used for restriction enzyme analysis of colonies, very efficiently released plasmid and genomic DNA.

We examined the affects of Triton X-100, Tween-20 and NP40 added to the Disperse or the Denature Solutions on plasmid DNA release. As shown in FIG. 13, the addition of 0.2% Triton X-100, Tween-20 or NP40 to the Denature Solution increased plasmid DNA release with Tween-20 yielding the best results. The addition of Tween-20 or NP40 to the Disperse Solution did not improve plasmid DNA release (data not shown).

One disadvantage to using 1% SDS in the Denature Solution is the formation of precipitates during storage. To avoid the formation of precipitates, SDS was substituted with 1% sarcosine in the Denature Solution. Sarcosine did not form precipitates in the Denature Solution during storage (data not shown) and produced less background in comparison to SDS treated samples (FIG. 14). However, sarcosine did not efficiently release plasmid DNA from strain XL1 blue or from bacterial glycerol stocks (data not shown).

Example 8

DNA Release and Analysis of Plasmid DNA from Bacterial Glycerol Stocks

This experiment demonstrates the release and analysis of plasmid DNA directly from bacterial glycerol stocks. Glycerol stocks of *E. coli* transformed with Clone A were prepared and stored frozen. The stock was then thawed and 0.5, 1.0, 1.5, 2.0 and 2.5 µl aliquots were combined with 0.5% Triton X-100, 10 mM Tris-HCl (pH 8.0) (Disperse Solution) to a final volume of 8 µl. Each sample then received 2 µl of Digest Mix (1 µl 10×RE buffer and 0.5 µl NheI and 0.5 µl XhoI) and was incubated at 37° C. for 30 minutes. For agarose gel electrophoresis, the samples were loaded onto 0.8% to 1.2% agarose gels and electrophoresed in 1×TAE or 1×TBE running buffer. The gel was then stained in 0.5 µg/ml ethidium bromide and the DNA was visualized by ultraviolet transillumination.

As shown in FIG. 15, plasmid DNA was released by restriction enzyme digestion and detected from as little as 0.5 µl of bacterial glycerol stock. Plasmid DNA was also released and detected from glycerol stocks by the chemical method described in Example 5.

Example 9

Direct Analysis of RNA

RNA was released from bacteria and directly analyzed by a modified chemical technique. A single isolated colony of *E. coli* transformed with Clone A DNA was picked from an transformation plate that had been cultured overnight. Colonies were suspended in 4 µl of 300 mM Tris-HCl (pH 8.0) (RNA Disperse Solution), mixed with an equal volume of 0.4% NaOH, 1% SDS (RNA Denature Solution), and electrophoresed on 1% agarose gel. As shown in FIG. 16, ribosomal 23S, 16S and 5S RNA were easily visualized using this technique.

Example 10

Direct Analysis of Genomic DNA

Four isolated colonies of *E. coli* strain DH10B that had been cultured overnight on agar plates were suspended 8 µl of 0.5% Triton X-100, 10 mM Tris-HCl. Each sample received 2 µl of Digest Mix (1 µl 10×RE buffer, 1 µl EcoRI) and was incubated at 37° C. for 16 hours. For agarose gel electrophoresis, the samples were loaded onto 0.8% to 1.2% agarose gels and electrophoresed in 1×TAE or 1×TBE running buffer. The gel was then stained in 0.5 µg/ml ethidium bromide and the DNA was visualized by ultraviolet transillumination.

As shown in FIG. 17, genomic DNA was efficiently released and analyzed by EcoRI digestion.

The foregoing description details specific methods which can be employed to practice the present invention. Having detailed such specific methods, those skilled in the art will well enough know how to devise alternative reliable methods at arriving at the same information in using the fruits of the present invention. Thus, however, detailed the foregoing may appear in text, it should not be construed as limiting the overall scope thereof; rather, the ambit of the present invention is to be determined only by the lawful construction of the appended claims. All documents cited herein are expressly incorporated by reference.

What is claimed is:

1. A method for releasing, separating and separately visualizing the presence of extrachromosomal DNA and genomic DNA in a microorganism said method comprising:

(a) suspending said microorganism in a first solution that causes lysis of said microorganism and the liberation of said extrachromocomal DNA and said genomic DNA from said microorganism so as to provide a first suspension;

(b) optionally heating said first suspension for at least 10 seconds at least 65° C.;

(c) combining said first suspension with a second solution comprising a restriction endonuclease so as to provide a second suspension, wherein said extrachromosomal DNA and said genomic DNA are digested, released and separately detectable from each other;

(d) detecting the presence of said extrachromosomal DNA and said genomic DNA in said second suspension, without prior separation of said extrachromosomal DNA and said genomic DNA from other cellular components.

2. The method according to claim 1, wherein said first solution comprises from about 0.1% (v/v) to about 5% (v/v) of a nonionic detergent.

3. The method according to claim 2, wherein said nonionic detergent is selected from the group consisting of Triton X-100, Tween-20, and NP40.

4. The method according to claim 2, wherein said nonionic detergent is Triton X-100.

5. The method according to claim 1, wherein said microorganism is selected from the group consisting of a bacterial cell, a yeast cell, a eukaryotic cell and a bacteriophage.

6. The method according to claim 1, wherein said microorganism is a bacterial cell.

7. The method according to claim 1, wherein step (d) is accomplished by a method that comprises gel electrophoresis.

8. The method according to claim 7, wherein said gel electrophoresis is capable of determining the size of said extrachromosomal DNA and said genomic DNA.

9. The method according to claim 1, which does not comprise the step of amplifying said extrachromosomal DNA and said genomic DNA by the polymerase chain reaction.

10. The method according to claim 1, wherein said first solution comprises Tris-HCl.

11. A method for releasing, separating and separately visualizing the presence of extrachromosomal DNA and genomic DNA in a microorganism said method comprising:

(a) suspending said microorganism in a solution comprising a restriction endonuclease, wherein said solution causes the lysis of said microorganism and the liberation of said extrachromocomal DNA and said genomic DNA from said microorganism and wherein said restriction endonuclease digests and releases said liberated extrachromosomal DNA and said genomic DNA, wherein said digested extrachromosomal DNA and said digested genomic DNA is separately detectable from each other, said step of suspending providing a suspension; and (b) detecting the presence of said extrachromosomal DNA and genomic DNA in said suspension, without prior separation of said extrachromosomal DNA and genomic DNA from other cellular components.

12. The method according to claim 11, wherein said solution comprises from about 0.1% (v/v) to about 5% (v/v) of a nonionic detergent.

13. The method according to claim 1, wherein said first solution does not comprise an endonuclease inhibiting amount of EDTA.

14. The method according to claim 11, herein said solution does not comprise an endonuclease inhibiting amount of EDTA.

* * * * *